(12) United States Patent
Pal et al.

(10) Patent No.: US 6,689,087 B2
(45) Date of Patent: Feb. 10, 2004

(54) FLOATING PROBE FOR ULTRASONIC TRANSDUCERS

(75) Inventors: Dharmendra Pal, Miami Lakes, FL (US); Thomas Peterson, Erie, PA (US)

(73) Assignee: Cybersonics, Inc., Erie, PA (US)

( * ) Notice: Subject to any disclaimer, the term of this patent is extended or adjusted under 35 U.S.C. 154(b) by 32 days.

(21) Appl. No.: 10/113,141

(22) Filed: Mar. 28, 2002

(65) Prior Publication Data

US 2002/0165470 A1 Nov. 7, 2002

Related U.S. Application Data

(60) Provisional application No. 60/279,427, filed on Mar. 28, 2001.

(51) Int. Cl.⁷ .............................................. A61B 17/00
(52) U.S. Cl. ...................................................... 604/22
(58) Field of Search .................... 604/22; 600/459; 606/1, 168, 169, 27; 601/2; 310/323.12, 0.18–0.19; 451/165; 408/17; 433/86, 119

(56) References Cited

U.S. PATENT DOCUMENTS

| | | | | |
|---|---|---|---|---|
| 3,619,671 A | * | 11/1971 | Shoh | 310/325 |
| 3,830,240 A | | 8/1974 | Antonevich et al. | 128/328 |
| 3,861,391 A | | 1/1975 | Antonevich et al. | 128/328 |
| 4,016,436 A | | 4/1977 | Shoh | 310/8.2 |
| 4,180,074 A | | 12/1979 | Murry et al. | 128/276 |
| 4,472,840 A | | 9/1984 | Jefferies | 3/1.9 |
| 4,537,511 A | | 8/1985 | Frei | 366/127 |
| 4,600,005 A | | 7/1986 | Hendel | 128/304 |
| 4,657,548 A | | 4/1987 | Nichols | 623/10 |
| 4,747,820 A | | 5/1988 | Hornlein et al. | 604/22 |
| 4,870,953 A | | 10/1989 | DonMicheal et al. | 128/24 |
| 4,881,761 A | | 11/1989 | Hornlein et al. | 285/239 |
| 4,951,653 A | * | 8/1990 | Fry et al. | 128/24 |
| 4,988,334 A | * | 1/1991 | Hornlein et al. | 604/22 |
| RE33,590 E | | 5/1991 | Dory | 128/660.03 |
| 5,111,822 A | * | 5/1992 | Dory | 128/660.03 |
| 5,152,763 A | * | 10/1992 | Johnson | 606/86 |
| 5,230,334 A | * | 7/1993 | Klopotek | 128/399 |
| 5,240,675 A | * | 8/1993 | Wilk et al. | 422/22 |
| 5,295,484 A | * | 3/1994 | Marcus et al. | 128/660.03 |
| 5,304,115 A | * | 4/1994 | Pflueger, Russell et al. | 604/22 |
| 5,344,435 A | * | 9/1994 | Turner et al. | 607/101 |
| 5,368,037 A | * | 11/1994 | Eberle et al. | 128/662.06 |
| 5,513,662 A | * | 5/1996 | Morse et al. | 128/898 |
| 5,549,638 A | | 8/1996 | Burdette | 607/97 |
| 5,551,448 A | | 9/1996 | Matula et al. | 128/897 |
| 5,556,379 A | | 9/1996 | Wolfinbarger | 604/49 |
| 5,597,345 A | * | 1/1997 | Young | 451/165 |
| 5,601,526 A | | 2/1997 | Chapelon et al. | 601/3 |
| 5,628,743 A | * | 5/1997 | Cimino | 604/22 |
| 5,657,760 A | | 8/1997 | Ying et al. | 128/660.03 |
| 5,695,500 A | | 12/1997 | Taylor et al. | 606/130 |
| 5,697,932 A | | 12/1997 | Smith et al. | 606/80 |
| 5,711,299 A | | 1/1998 | Manwaring et al. | 128/653.1 |
| 5,725,478 A | | 3/1998 | Saad | 600/157 |

(List continued on next page.)

*Primary Examiner*—Francis J. Jaworski
(74) *Attorney, Agent, or Firm*—The Bilicki Law Firm, P.C.

(57) ABSTRACT

The present invention relates to a novel device with an ultrasonic based drill and corer. The invention uses ultrasonic and subsonic vibrations, which is produced by a frequency compensation coupler or free mass, to produce the hammering action with relatively low axial-force required. The invention can also be fitted with irrigation and aspiration capabilities. The invention is furnished with a body sensor-feedback apparatus, which provide feedback to the operator as to the optimal frequency and power use of the generator. The assembly presented also has a coolant jacket to keep the drill or coring apparatus at optimum temperature prolonging the life of the instrument and the quality of the sample. The invention can be used in numerous applications one of such notable application is on the field of orthopedics.

1 Claim, 9 Drawing Sheets

U.S. PATENT DOCUMENTS

| | | | |
|---|---|---|---|
| 5,730,372 A | 3/1998 | Bradley | 241/29 |
| 5,730,719 A | 3/1998 | Edwards | 604/22 |
| 5,779,644 A | 7/1998 | Eberle et al. | 600/463 |
| 5,797,871 A | 8/1998 | Wolfinbarger, Jr. | 604/49 |
| 5,810,765 A | 9/1998 | Oda | 604/31 |
| 5,820,581 A | 10/1998 | Wolfinbarger, Jr. | 604/49 |
| 5,871,514 A | 2/1999 | Wiklund et al. | 607/36 |
| 5,871,515 A | 2/1999 | Wiklund et al. | 607/36 |
| 5,897,578 A | 4/1999 | Wiklund et al. | 607/36 |
| 5,902,264 A | 5/1999 | Toso et al. | 604/27 |
| 5,919,215 A | 7/1999 | Wiklund et al. | 607/36 |
| 5,938,615 A | 8/1999 | Eberle et al. | 600/463 |
| 5,950,629 A | 9/1999 | Taylor et al. | 128/897 |
| 6,022,354 A | 2/2000 | Mercuri et al. | 606/80 |
| 6,045,555 A | 4/2000 | Smith et al. | 606/80 |
| 6,080,155 A | 6/2000 | Michelson | 606/61 |
| 6,204,592 B1 * | 3/2001 | Hur | 310/323.12 |

* cited by examiner

FLOATING PROBE FOR ULTRASONIC TRANSDUCERS

This application is a conversion of U.S. Provisional Patent Application Serial No. 60/279,427 filed Mar. 28, 2001. This application does not claim priority to co-pending U.S. patent application Ser. No. 09/518,801 filed Mar. 3, 2000 entitled "Method and Apparatus for Cleaning Medical Instruments and the like".

BACKGROUND OF THE INVENTION

FIELD OF THE INVENTION

The present invention relates to a novel system with an ultrasonic based drill and corer. More particularly, the invention uses a combination of ultrasonic and sonic vibrations to produce a hammering effect with relatively low axial-force. In addition, the invention relates to orthopedic applications such as bone grafting and hip replacement. Also, the invention can be used in applications such as brain shunt cleaning that require irrigation and aspiration capabilities. The present invention also has a body sensor-feedback apparatus, which provides feedback to the operator as to the optimal frequency and power use of the ultrasonic generator.

BACKGROUND OF THE INVENTION

Many applications require effective drilling and coring to make holes or extract materials. Such applications can include but are not limited to planetary exploration, military, medical operations, and geologic exploration. Existing drilling and coring techniques for these applications are limited by the need for large axial forces, great power consumption, and the use of a heavy mechanism to accomplish the drilling or coring. Drilling a small hole or coring a small sample of material is difficult because the large axial forces required to drill through or core the material. Other areas of concern associated with conventional drills is the need for high axial load and that they are subject to drill tip jamming, breaking, dulling and are difficult to use in drilling non-horizontal or hard surfaces. For example, non-horizontal or hard surfaces require the use of large and heavy platforms to support the drill. The drilling process can also be hampered by the accumulation of drilling debris in the drilling area.

The invention disclosed hereby can drill through all sorts of materials and can be used for biomedical applications such as bone grafts or use for geological studies. Although prior art shows or suggest various methods or apparatus for bone grafting, irrigation and aspiration during procedures and sensing mechanism, it is apparent to those skilled in the art that more efficient and easier methods are desirable. The present invention provides the needed improvements over the prior art. In addition, it will be apparent that this invention is well suited for very diverse applications from planetary exploration to medical operations.

SUMMARY OF THE INVENTION

The present invention provides an apparatus that uses a combination of ultrasonic and subsonic vibrations to perform effective drilling and coring. The device can be used for multiple applications in which drilling and/or coring is required. The present invention presents a low power, misalignment-tolerant device that exhibits a self-extracting debris process. The device can be further modified to include irrigation and aspiration capabilities.

DETAILED DESCRIPTION OF THE PREFERRED EMBODIMENT

Figure 1A:
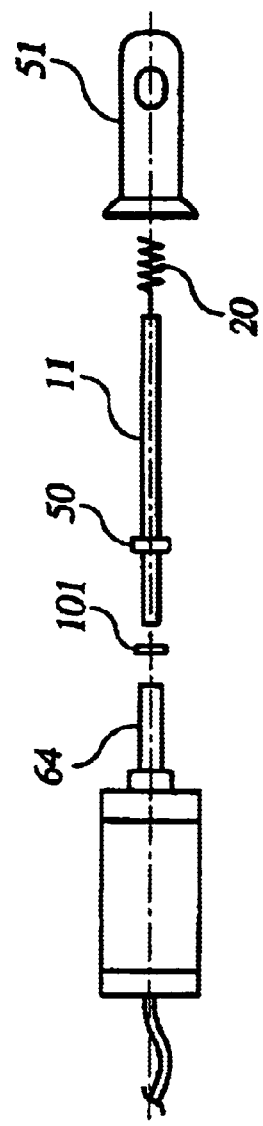
FIGS. 1a and 1b depict the components of the invention in an exploded fashion in the order in which the components are fitted together.

Referring now to the drawings in detail, for ease of the reader, like reference numerals designate identical or corresponding parts throughout the views depicted in the drawings. It should be noted that a drawing does not depict each embodiment of the present invention; nor is each of the notable applications of the present invention depicted by a drawing. The device uses a floating-head drilling mechanism, where high frequency ultrasonic vibrations are induced by an ultrasonic generator.

Figure 1B:
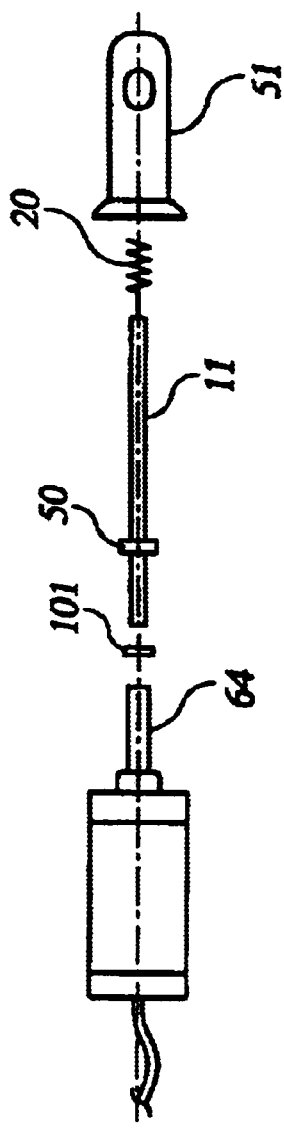
Figure 5B:
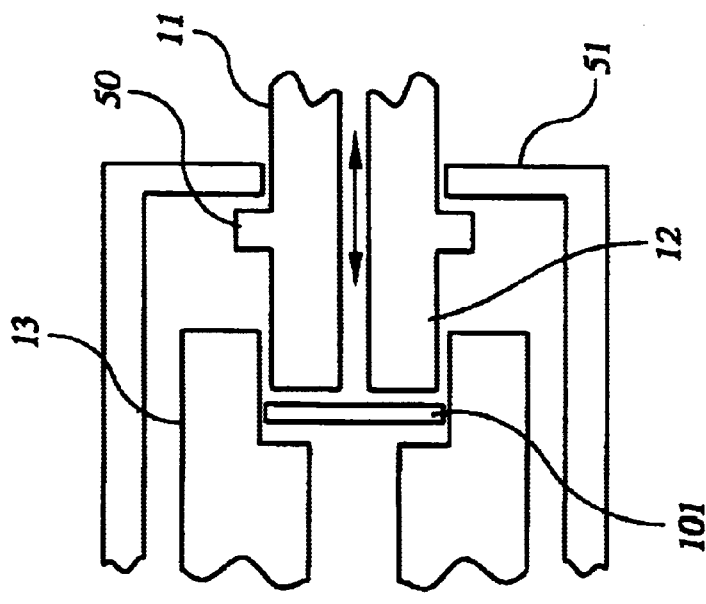
FIGS. 5A and 5B show another cross sectional view of a section of the ultrasonic floating tip that illustrates the frequency compensation coupler or free mass.
Figure 5A:
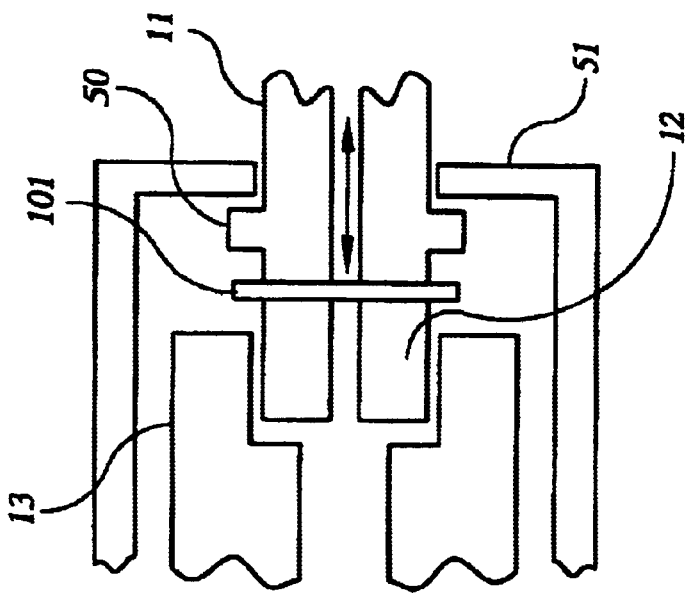

FIG. 1 shows the present invention. The ultrasonic frequencies are generated by a piezoelectric stack actuator 60, shown in FIG. 2a. The high frequency vibrations generated by the generator are enhanced by an ultrasonic horn 64. Probe 11 or drill bit is inserted into horn 64, which, in turn, is driven by the generator. Probe 11 is not, however, fixedly secured to horn 64. Barrier member 51 covers horn 64 and possesses an opening large enough for the probe tip 11 to fit through. Probe 11 also has capturing member 50 that is fitted on probe 11 closer to the end of probe 11 that is to be inserted into horn 64. Capturing member 50 is larger that the opening in barrier member 51 and prevents probe 11 from disengaging horn 64 completely. Thus, capturing member 50 is located between horn 64 and barrier member 51. This construction is also shown in FIGS. 5a and 5b. This is called a floating probe because probe 11 actually disengages from horn 64 during the ultrasonic frequency cycles. However, probe 11 can only disengage so much since the combination of the capturing member and the barrier member prevent the probe from disengaging completely. In addition, spring 20 can be utilized with the present invention. Spring 20 is located between capturing member 50 and barrier member 51 and provides extra force in pushing probe 11 (and the capturing member) back into horn 64 after the probe disengages the horn.

The barrier member can take many geometric shapes, two of which are shown in the drawings of this application. However, one of ordinary skill in the art will readily appreciate that the barrier member could take many different geometric shapes so long as the barrier member has the opening to allow the probe to fit through and provides a surface to stop the capturing member (and the probe) from completely disengaging from the horn.

FIG. 1 also depicts the free mass or frequency compensation coupler 101 that can be used with present invention to enhance the conversion of the ultrasonic frequencies to subsonic frequencies. The frequency compensation coupler or free mass 101 is a metal disk that slidably engages probe 11. One of ordinary skill in the art should appreciate that other materials of various shapes could be used in the construction of frequency compensation coupler 101. Frequency compensation coupler 101 is located between the capturing member of probe 11 and the end of probe 11 that fits horn 64. Frequency compensation coupler 101 converts ultrasonic action to subsonic action. This is desirable in some applications because the subsonic action creates less heat and friction than ultrasonic action. The phrase "free mass" as used herein is defined as a piece of material (metal or otherwise) that is not physically attached to any other component. Frequency compensation coupler or free mass 101 is located between the horn 64 and the proximal end of the ultrasonic probe 11, and is used to enhance the jack-hammering effect of the ultrasonic drill/corer for certain applications. Horn 64 amplifies the ultrasonic vibrations that are induced by ultrasonic generator. The free mass oscillates between the horn and the capturing member of the probe.

One of ordinary skill in the art will readily appreciate that frequency compensation coupler 101 can vary in size, shape and weight. The factors depend on the size of transducer horn 64, probe 11 and on the frequency output at which the device is to be operated. For applications such as drilling hardened materials, as described herein, the free mass is optimally ¼ inch in diameter. However, one of ordinary skill in the art will appreciate that the diameter of free mass 101 is dependent on the size of horn 64 and probe 11. For applications such as the removal of pacemaker leads, free mass 101 is also optimally ¼ inch in diameter. However, in this application, the diameter of the probe is dependent on the diameter of the lead to be removed. Thus, the free mass, in this particular application, is also a function of the lead to be removed.

Figure 2A:
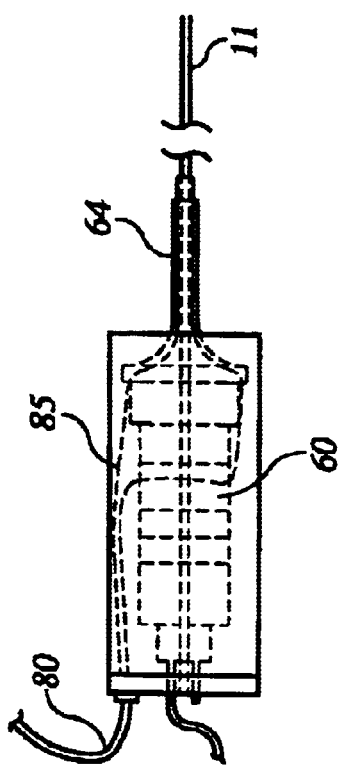
FIGS. 2a and 2b show a cross sectional views of the ultrasonic floating probe with the internal and external cooling jacket and condom.

FIG. 2a shows the piezoelectric crystals that generate the ultrasonic frequencies that emanate to the horn. FIG. 2a also depicts an internal cooling jacket 85 which can be extended over the crystals or restricted only to the horn area.

Figure 2B:
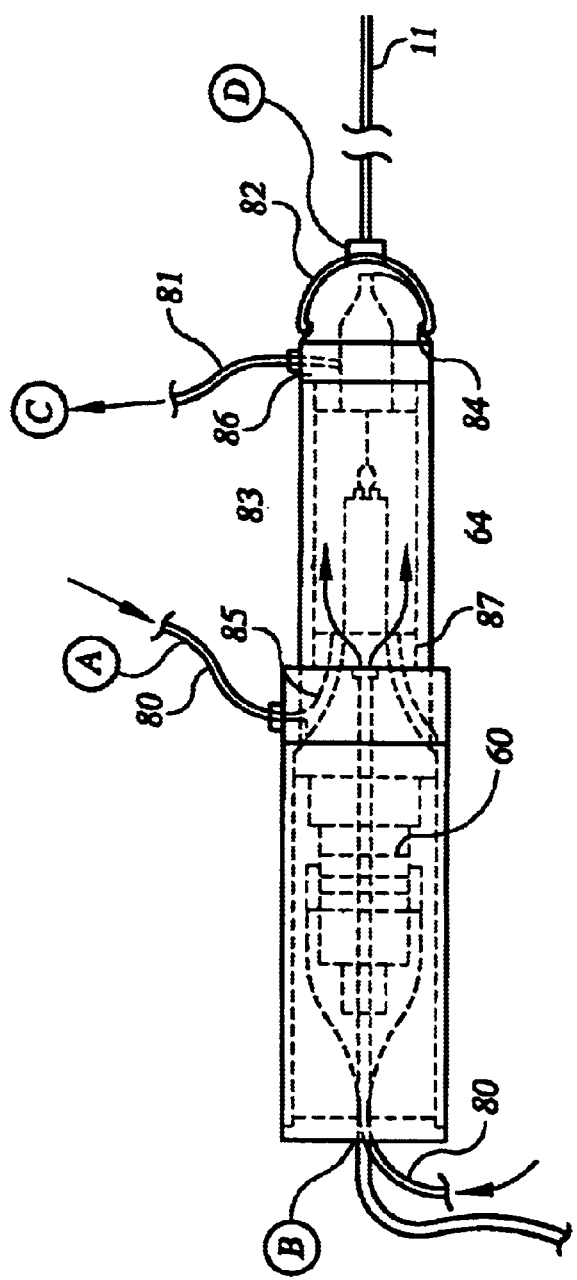

FIG. 2b shows probe 11 with internal cooling jacket 85. Internal cooling jacket 85 requires that horn 64 have a solid top or barrier 87 between probe 11 and the bottom of horn 64 so that fluid can be injected through catheter 80 against the solid top to cool down the probe and horn. Internal cooling jacket 85 can be extended toward piezoelectric ceramics 60 or restricted only to horn 64 area. FIG. 2b depicts a probe with internal cooling jackets 85 and external cooling jackets 83. Internal cooling jacket 85 as explained above requires that horn 64 have a solid top or barrier 87 between probe 11 and the bottom of horn 64. The fluid coolant is pulsed at solid top 86 and flows back out around the sides of the catheter. The housing of external cooling jacket 83 is placed over probe 11 and horn 64 so that probe 11 and horn 64 are constantly receiving cool fluid. The cool fluid is added through catheter 81. Also an internal and external coolant condoms 82 are depicted on the figure. The internal and external coolant condoms and fittings are present in the invention to prevent coolant from leaking from the apparatus. These coolant condoms are only necessary with the use of the external cooling jacket. The internal coolant condom is a silicon disc that is placed along the interior of the top of the external cooling jacket. External coolant condom 82 is a piece of finger cotton that is stretched over the top of probe 11 and external-cooling jacket 83. Piezoelectric crystals 60 can also be observed in this figure.

FIG. 2b depicts the two methods of cooling the device. As shown in FIG. 2b, water can enter at either point A or point B. The water flows around the device, cooling the device as the water swirls around. The water then exits through point C. In addition, FIG. 2b shows that a fitting D can replace the external coolant condom to keep the water from flowing along the length of the probe.

Figure 3:
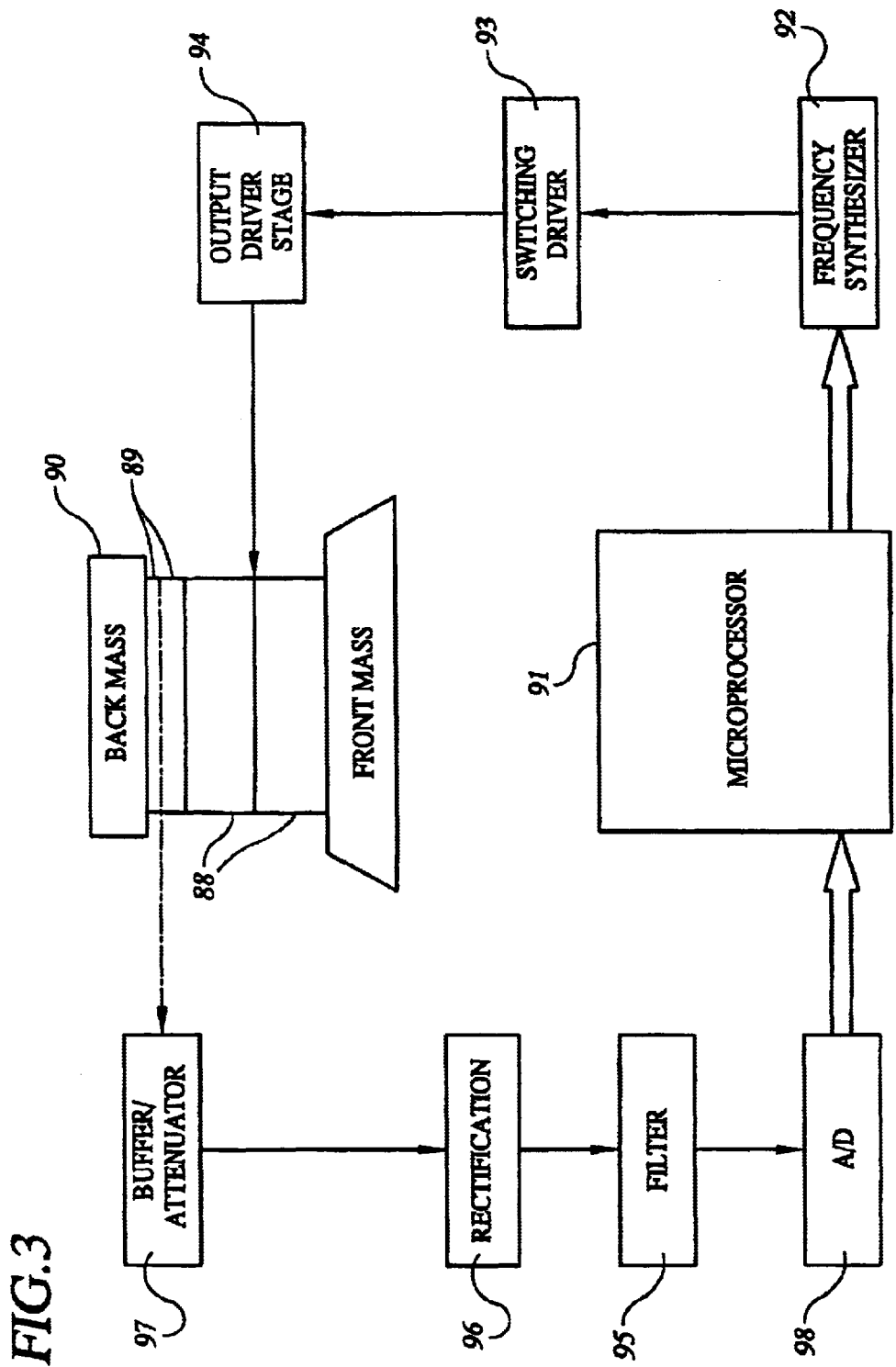
FIG. 3 shows a flowchart for the feedback loop for displacement sensing of the body sensor.

FIG. 3 shows a flowchart for the feedback loop for displacement sensing of the body sensor. The feedback loop is provided to the operator as to the optimal frequency and power use of the generator. To enable the feedback, at least two thin piezoelectric crystals 89, which will function as sensing ceramics, will be placed near big piezoelectric crystals 88, or driving ceramics. When driving ceramics 88 are energized, they will put a force on sensing ceramics 89. This force is translated to an electrical signal and sent to microprocessor 91. The translation of the force is accomplished by attenuator 97, rectification 96, filter 95 and A/D source 98. Microprocessor 91 then calculates the frequency and power outputs and can adjust the frequency and power output to the user's requirements. The required change in frequency is done by frequency synthesizer 92, and a change in power by output driver stage 94. This device provides an instantaneous reading as to the optimal settings under which the transducer assembly should operate. This allows the transducer assembly to stay in tune throughout the use of the transducer.

Figure 4B:
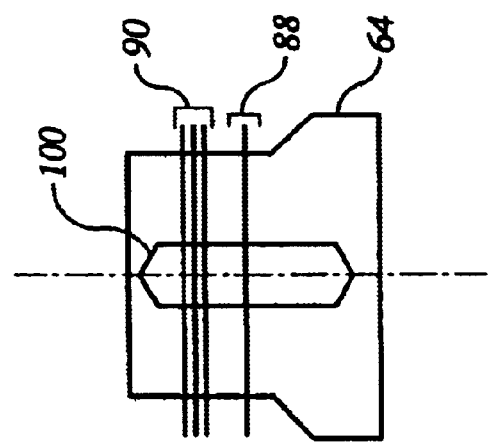
FIGS. 4a and 4b shows a cross sectional view of a section of the ultrasonic floating probe that illustrates the piezoelectric sensing crystals.
Figure 4A:
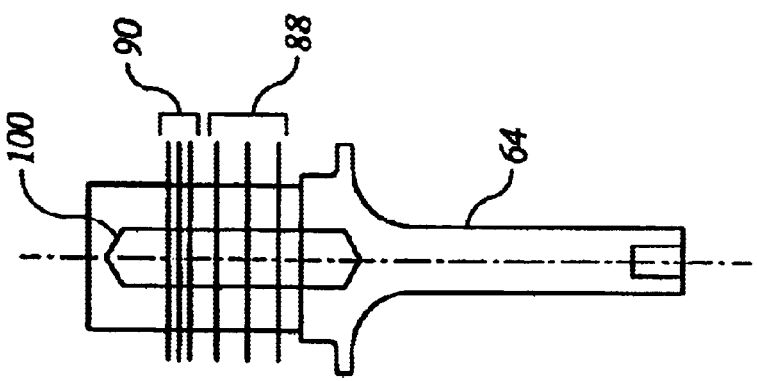

FIGS. 4a and 4b show a cross sectional view of a section of the ultrasonic floating probe that illustrates piezoelectric sensing crystals 90 in connection with body sensor feedback apparatus described and shown in FIG. 3. FIG. 4 illustrates the location and connection between the driving crystals, which produce the ultrasonic frequencies, the sensing crystals, which provide the feedback to the microprocessor, in the context of an ultrasonic device as contemplated by the present invention. Piezoelectric sensing ceramics 90 are very thin in comparison with piezoelectric driving ceramics 88. The encased biasbolt 100 and horn 64 can also being appreciated in the figure. The stepped horn 64 shape offers the greatest displacement magnification when compared to other geometries of horns. The biasbolt or stress bolt 100 is used contain the transducer assembly and maintain the strength of the piezoelectric ceramics. If a drill/corer head with a hollow center to create a coolant path is desired the bolt can be replaced with a threaded tube either placed at the center of the piezoceramics stack or, in an alternative embodiment, external to the stack encircling the sandwich piezoceramics. Driving ceramics 88 when energized will put a force on thin piezoelectric crystals 90. This force will be translated into electrical signals, which will result in a feedback providing instantaneous readings with optimal settings under which the transducer assembly should operated.

FIG. 5a shows another cross sectional view of a section of the ultrasonic floating tip that illustrates the frequency compensation coupler. In this close up view of the proximal end of ultrasonic probe 11 the tip of transducer 13 can be observed in relationship with frequency compensation coupler or free mass 101. The frequency compensation coupler or free mass is a metal disk or other suitable material. Frequency compensation coupler or free mass 101 fits over floating probe 11 and is located between capturing member 50 of probe 11 and end of the probe 12 that fits into the horn.

The free mass or frequency compensation coupler can also be located inside an annular probe between the portion of the probe where the capturing member is located and the horn. Free mass 101 or frequency compensation coupler can also be located between the capturing member of the probe and the horn as shown in FIG. 5b. One of ordinary skill in the art will note that other arrangements between the probe, the capturing member, the free mass and the horn can be envisioned. The present invention contemplates such envisioned arrangements. In addition, more than one frequency compensation coupler or free mass can be used.

Frequency compensation coupler 101 is made of a strong material, preferably metal, since it may be the weakest member of the ultrasonic probe assembly. The preferred materials are stainless steel, titanium, or other similar materials. However, one of ordinary skill in the art will readily appreciate that other materials may be used with this device. Frequency compensation coupler or free mass 101 reduces probe frequency from kHz to Hz. Thus, the frequency compensation coupler converts ultrasonic action into subsonic. This is desirable in some applications because the subsonic action creates less heat and performs better than an ultrasonic frequency.

FIG. 5b illustrates cross sectional view of a section of the ultrasonic floating tip with the free mass. In close up view of the proximal end of annular ultrasonic probe 11, the tip of transducer 13 can be observed in relationship with the frequency compensation coupler or free mass 101. The free mass is generally a metal disk but other materials can be used as long as strength is sufficient. The free mass is located between the tip of the transducer and the end of floating probe 11. The function of the free mass 101 is to enhance the jack hammering effect of the ultrasonic drill/corer.

FIG. 6 shows different assemblies of the ultrasonic floating probe. In FIG. 6a a handheld assembly with a one-piece annular plastic probe 11 inserted into horn 64 is shown. It is possible to have a handheld assembly due to the relatively low axial preload required and because it is insensitive to alignment and can perform angle drilling and coring. The drilling or coring mechanism is the result of transverse and longitudinal motions such as hammering, which reduces the chances of having tip 119 jamming. Tip 119 of probe 11 doesn't have to be sharp and a diversity of tips can be design to the take advantage of this. FIG. 6b illustrated the same assembly except it also shows the frequency compensation coupler explained in FIG. 5a. FIG. 6c shows the same handheld assembly with the addition of the frequency compensation coupler or free mass. If the hammering effect is to be enhanced without affecting the ultrasonic frequency, free mass 101 could be added to the assembly as shown in FIG. 6d.

Figure 6A:
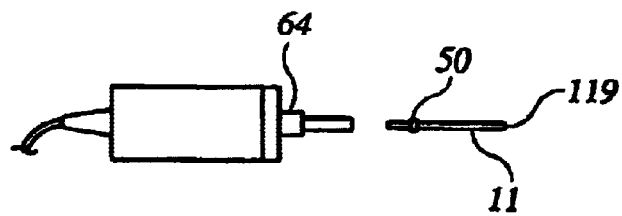
FIGS. 6a, b, c, and d show different assemblies for the ultrasonic floating probe.
Figure 6B:
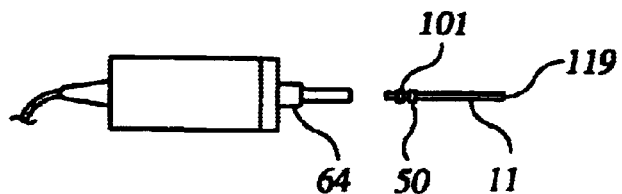
FIG. 6e depicts a multiple piece plastic probe.
FIG. 6f depicts a one-piece plastic probe
Figure 6C:
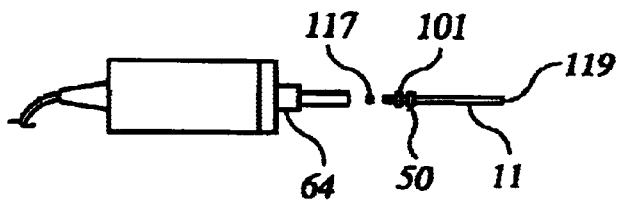
Figure 6D:
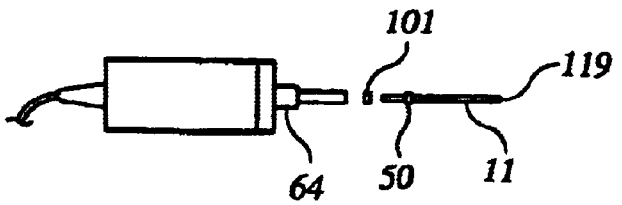
Figure 6E:
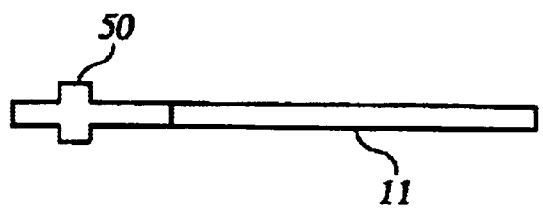
Figure 6F:
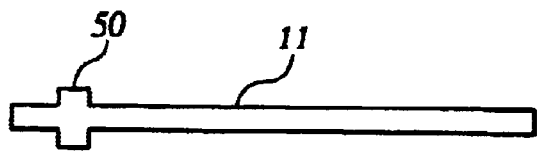

Furthermore, FIG. 6e depicts a two or multiple piece probe, while FIG. 6f depicts a one-piece probe. It should be noted that in the two or multiple piece construction, the pieces can be made of the same materials or can be made of varying materials such as stainless steel, titanium, plastic, or other suitable hardened material. It should also be noted that the one-piece construction could be made of plastic, stainless steel, titanium, or other suitable hardened material.

Figure 7A:
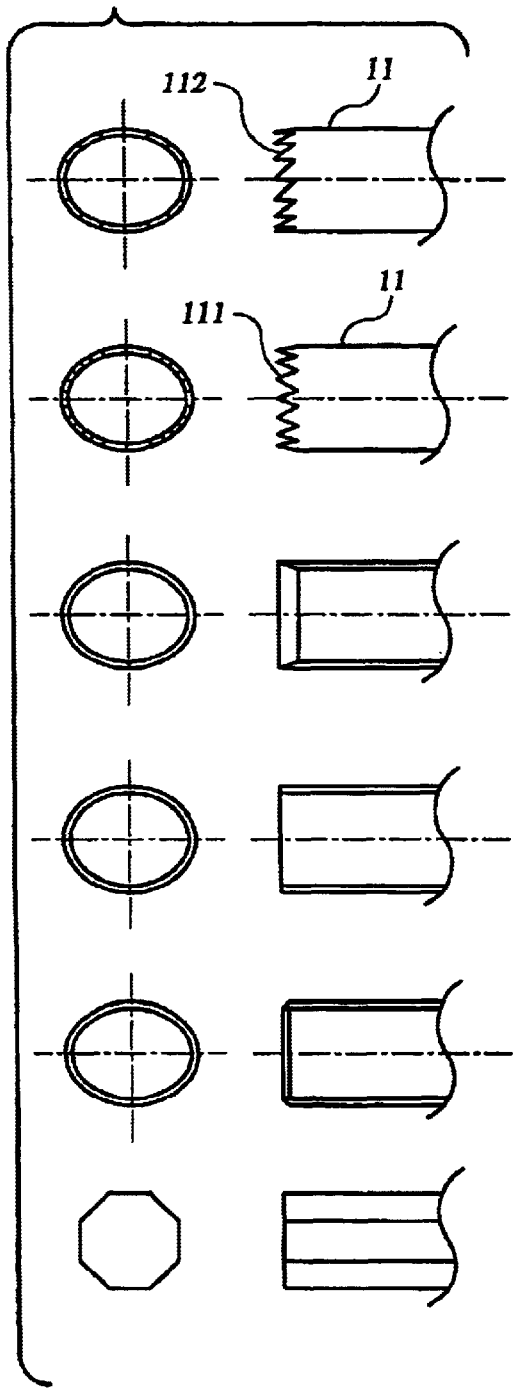
FIGS. 7A and 7B show a series of tip configurations that can be used on the ultrasonic floating probe according to the application.
Figure 7B:
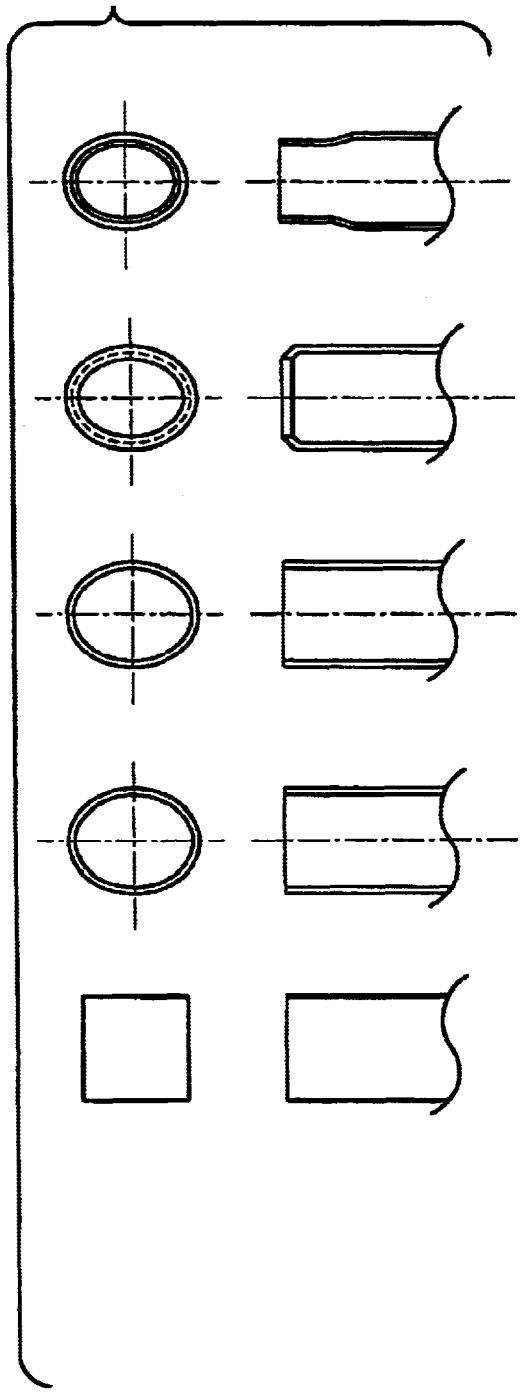

FIGS. 7A and 7B show a series of tip configurations that can be used on the ultrasonic floating probe according to the application. The tips could be constructed as closely spaced small diameter rods to allow chipping selected sections of the material being work on, or be smooth for slicing. Since the tip and the whole probe don't turn, drilling sensors can be added near the tip to examine the cored material. Potential sensors include temperature, eddy-current, acoustic sensors, dielectrics, fiber optics and others. Tip configurations 111 and 112 are shown which have a fingered construction for coring. The fingered configuration is particularly well suited for the coring of bones, one of the preferred uses of this ultrasonic assembly. It will be obvious to one of ordinary skill in the art that any type of tip configuration can be used with the present invention.

Figure 8:
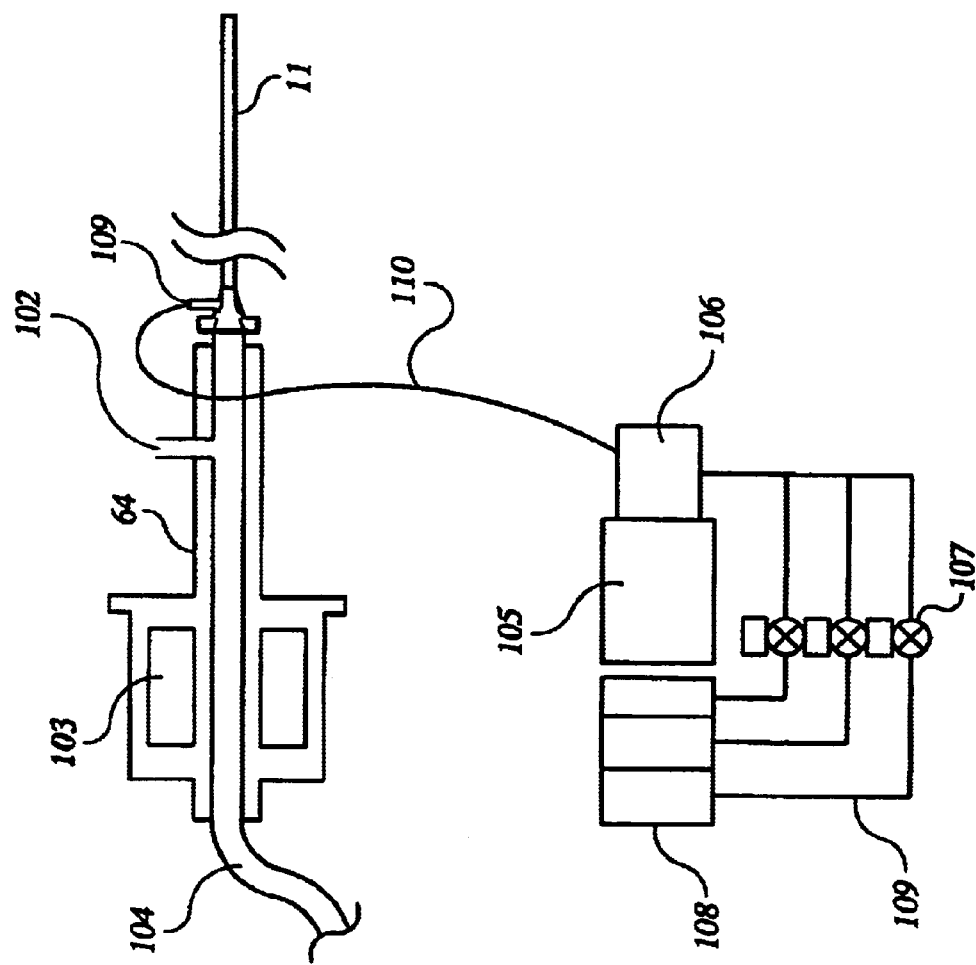
FIG. 8 shows a cross sectional view of the ultrasonic floating probe with irrigation and aspiration capabilities.

FIG. 8 shows a cross sectional view of the ultrasonic floating probe with irrigation and aspiration capabilities. The figure illustrates a free-floating annular probe or corer 11. At the proximal end of free floating corer 11 there is an adapter 109 for irrigation. Adapter 109 has conduit 110, which is connected to pump head 106. Pump head 106 is part of pump 105, which will pump irrigation fluid into corer 11. The pump assembly has a number of tanks 108, which will contain irrigation fluids such as saline. Each tank 108 has a conduit that goes to a series of solenoids 107 and then to main pump head 106. There are two vacuum exits one for sampled cored 104 and another 102 for dust and volatile. These two sets of vacuum exits composed the aspiration unit. One of vacuum exits 102 is present in stepped horn 64 and the other at the back of the assembly, behind piezoelectric stacks 103.

Figure 9:
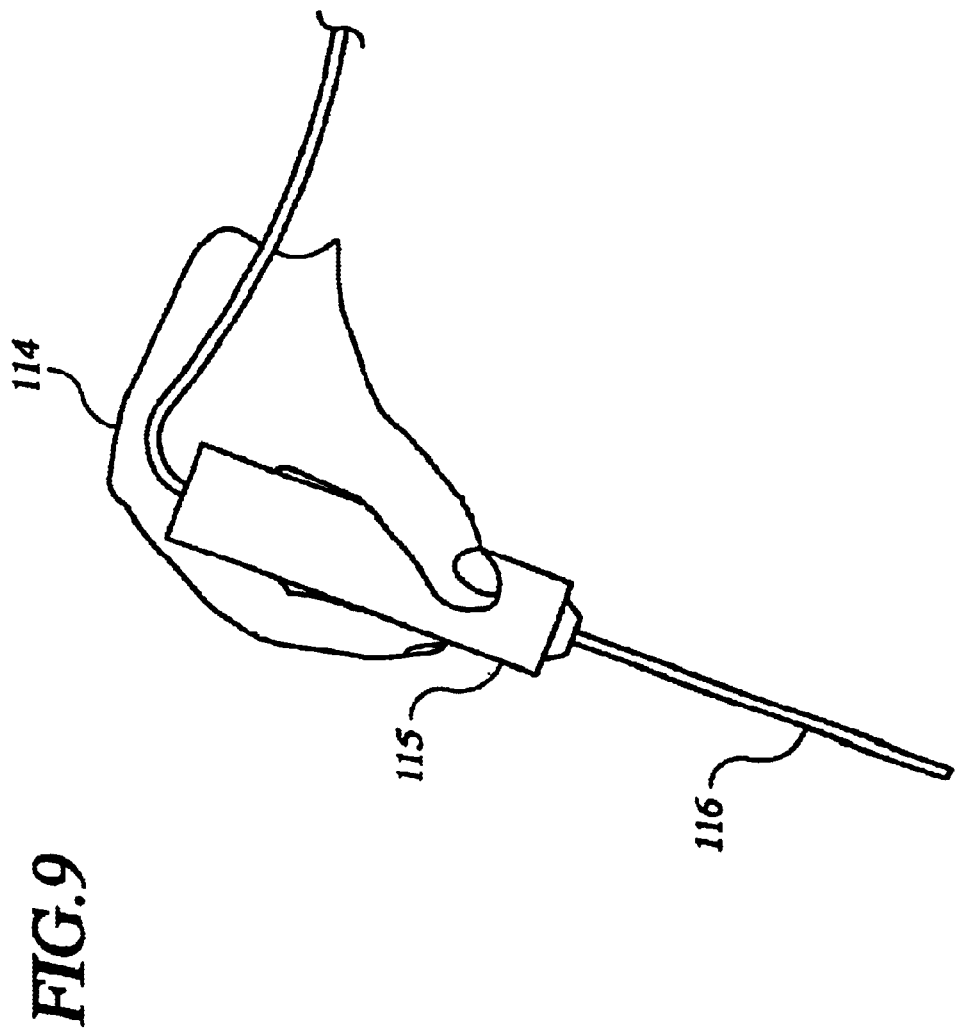
FIG. 9 illustrates the ease of use of the ultrasonic floating probe during drilling or coring.

FIG. 9 illustrates the ease of use of the ultrasonic floating probe during drilling or coring. FIG. 9 shows hand 114 of the user and demonstrates the ease of holding the invention due to the low axial force required to produce the hammering or drilling action. The closed and lightweight handle 115 with the transducer, horn, etc can be appreciated on the figure. Floating probe 116 used for coring and/or drilling can be observed. Probe 116 can be of different lengths depending upon the application.

It is obvious to one skilled in the art that this invention, in any of the embodiments described above, can be used in many applications. A notable application of the subject invention is on bone grafts. The preparation of autogenous bone graft, allografts, or other substitutes such as corralline hydroxyapatite the present invention can be of use.

One of the steps in bone graft is the extraction of the material to be grafted. The use of the present invention with its coring and sample extraction mechanisms is especially adapted for this purpose. Another bone graft technique is the use of demineralized bone. Demineralized bone as used herein is defined as a cortical allograft bone wherein the removal of surface lipids and dehydration of the bone has been accomplished by diverse solutions such as ethanol or hydrochloric acid. The demineralization removes acid soluble proteins and leaves behind acid-insoluble protein, bone growth factors and collagen. The bone treated in this manner can be implanted in strips or processed into smaller particles. Also it has been suggested that if holes are drilled into cortical allograft it can increase the porosity of the bone by allowing a more efficient demineralization. This can result in a bone graft that it is more osteoconductive and osteoinductive. In all of these procedures the invention presented can be of great use. Another use for orthopedic drilling is on hip replacement where a hole must be drilled in the hip that is going to be replaced in preparation for the replacement. Bone marrow samples can also be obtained out of a person's healthy bone for typing or transplant in a less painful way that other procedures presented on the art.

Another orthopedic use is for the drilling/coring for insertion of pins or screws after an accident or disease to put together and repair the bone of a patient.

The transducer assembly can drill through different materials, including but not limited to, basalt, corsite, chalk, and ice. Uses in mining operations and sample taking on interplanetary explorations are notable applications of the present invention.

Although, for convenience, the method and resultant apparatus of the present invention has been described hereinabove primarily with respect to its preferred embodiments, it will be apparent to those skilled in the art that many variations of this invention can be made without departing from the spirit of the invention as claimed. The description presented in the preferred embodiments is not intended to demonstrate all of the possible arrangements and modifications to the design. For those skilled in the art, changes will be apparent that will fall within the spirit and the scope of the present invention.

What I claim is:

1. An ultrasonic drill comprising:
   a resonator probe, said probe having a proximal end and a distal end;
   a capturing member on said resonator probe;
   an ultrasonic generator, said generator having a plurality of piezoelectric ceramic elements adapted to receive the proximal end of said resonator probe;
   a barrier member adapted to receive said probe;
   a horn integral to said generator;
   a frequency compensation coupler slidably engaged to said resonator probe, said frequency compensation coupler located between said capturing member and said horn;
   an internal cooling jacket, and
   a catheter.

* * * * *